US 6,559,133 B2

(12) United States Patent
Mruk (10) Patent No.: US 6,559,133 B2
(45) Date of Patent: May 6, 2003

(54) USE OF FLAVONE 8-ACETIC ACID IN VASCULAR AND CARDIOVASCULAR INTERVENTIONS AND ACUTE CORONARY SYNDROMES

(76) Inventor: Jozef S. Mruk, P.O. Box 762166, Wichita, KS (US) 67278-2166

( * ) Notice: Subject to any disclaimer, the term of this patent is extended or adjusted under 35 U.S.C. 154(b) by 0 days.

(21) Appl. No.: 09/767,621

(22) Filed: Jan. 23, 2001

(65) Prior Publication Data

US 2001/0041687 A1 Nov. 15, 2001

Related U.S. Application Data

(60) Provisional application No. 60/178,088, filed on Jan. 24, 2000.

(51) Int. Cl.[7] ..................... A61K 31/727; A61K 31/352
(52) U.S. Cl. ......................... 514/56; 514/456; 514/822; 514/824; 514/834; 435/7.21; 424/85.2; 424/183
(58) Field of Search ................................. 514/456, 822, 514/824, 834, 56; 435/7.21; 424/85.2, 183

(56) References Cited

U.S. PATENT DOCUMENTS

| | | | |
|---|---|---|---|
| 2,897,211 A | 7/1959 | P. da Re | 260/345.2 |
| 2,921,070 A | 1/1960 | P. da Re | 260/247.2 |
| 3,812,156 A | 5/1974 | Bonola et al. | 260/345.2 |
| 4,057,641 A | 11/1977 | Appleton et al. | 424/283 |
| 4,122,200 A | 10/1978 | Briet et al. | 424/275 |
| 4,602,034 A | 7/1986 | Briet et al. | 514/456 |
| 4,783,533 A | 11/1988 | Briet et al. | 514/456 |
| 4,791,136 A | 12/1988 | Batchelor et al. | 514/456 |
| 4,904,690 A | 2/1990 | Aono et al. | 514/456 |
| 5,061,488 A | 10/1991 | Wiltrout et al. | 424/85.2 |
| 5,096,707 A | 3/1992 | Wiltrout et al. | 424/195 |
| 5,118,684 A | 6/1992 | Attwood et al. | 514/337 |
| 5,126,129 A | 6/1992 | Wiltrout et al. | 424/85.2 |
| 5,227,368 A | 7/1993 | Gerlach et al. | 514/12 |
| 5,238,954 A | 8/1993 | Aristoff | 514/456 |
| 5,585,243 A | 12/1996 | Aster et al. | 435/7.21 |
| 5,756,538 A | 5/1998 | Cassels et al. | 514/456 |

FOREIGN PATENT DOCUMENTS

| | | |
|---|---|---|
| JP | 59076079 | 4/1984 |
| JP | 59076080 | 4/1984 |
| JP | 59222486 | 12/1984 |
| WO | WO 2001052839 | 7/2001 |

OTHER PUBLICATIONS

Mruk et al., "Antithrombotic efficacy of low–molecular weight heparin in deep arterial injury." Arterioscler. Thromb. 12(2), pp. 250 255, 1992.

(List continued on next page.)

Primary Examiner—Samuel Barts
Assistant Examiner—Devesh Khare
(74) Attorney, Agent, or Firm—Christie, Parker & Hale, LLP (57) ABSTRACT

A method for treatment of a vascular or cardiovascular condition or acute coronary syndromes comprises administering an effective amount of a flavone 8-carboxylic acid to a mammal suffering from a vascular or cardiovascular condition or acute coronary syndromes. The flavone 8-carboxylic acid is typically flavone 8-acetic acid. The flavone 8-carboxylic acid can be administered alone or in combination with another agent such as a thrombolytic agent, an antithrombotic agent, an anticoagulant, or an antiplatelet agent. The invention also includes pharmaceutical compositions formulated for the treatment of a vascular or cardiovascular condition or acute coronary syndromes.

23 Claims, 3 Drawing Sheets

OTHER PUBLICATIONS

D.R. Phillips et al., "The Platelet Membrane Glycoprotein IIb–IIIa Complex," *Blood* 71:831–843 (1988).

M.H. Kroll & A.I. Schafer, "Biochemical Mechanisms of Platelet Activation," *Blood* 74: 1181–1195 (1989).

P.S. Frenette & D.D. Wagner, "Molecular Medicine: Adhesion Molecules—Part I," *New Eng. J. Med.*. 334: 1526–1529 (1996).

P.S. Frenette & D.D. Wagner, "Adhesion Molecules—Part II: Blood Vessels and Blood Cells," *New Eng. J. Med.* 335: 43–45 (1996).

J. Lefkovits & E.J. Topol, "The Clinical Role of Platelet Glycoprotein IIb/IIIa Receptor Inhibitors in Ischemic Heart Disease," *Cleve. Clin. J. Med.* 63: 181–189 (1996).

R.C. Becker, "Antiplatelet Therapy," *Science & Medicine* 3: 12–21 (1996).

Z.M. Ruggeri, "Mechanisms Initiating Platelet Thrombus Formation," *Thrombosis & Hemostatis* 78: 611–616 (1997).

D.J. Kerr & S.B. Kaye, "Flavone Acetic Acid—Preclinical and Clinical Activity," *Eur. J. Cancer Clin. Oncol.* 25: 1271–1272 (1989).

J. Rubin et al., "Flavone–8–Acetic Acid Inhibits Ristocetin–Induced Platelet Agglutination and Prolongs Bleeding Time," *Lancet* 2: 1081–1082 (1987).

G.P. Smith et al., "Flavone Acetic Acid (NSC 347512) Induces Hemorrhagic Necrosis of Mouse Colon 26 and 38 Tumors," *Eur. J. Cancer Clin. Oncol.* 23: 1209–1211 (1987).

S. Hill et al., "Vascular Collapse After Flavone Acetic Acid: A Possible Mechanism of Its Anti–Tumor Action," *Eur. J. Cancer Clin. Oncol.* 25: 1419–1424 (1989).

J.C. Murray et al., "Flavone Acetic Acid Induces a Coagulopathy in Mice," *Br. J. Cancer* 60: 729–733 (1989).

G. Thurston et al., "Anticoagulant Treatment Does Not Affect the Action of Flavone Acetic Acid in Tumor–Bearing Mice," *Br. J. Cancer* 64: 689–692 (1991).

J.C. Murray et al., "Selective Induction of Endothelial Cell Tissue Factor in the Presence of a Tumor–Derived Mediator: A Potential Mechanism of Flavone Acetic Acid Action in Tumor Vasculature," *Int. Cancer* 49: 254–259 (1991).

J.C. Murray et al., "Flavone Acetic Acid Potentiates the Induction of Endothelial Procoagulant Activity by Tumor Necrosis Factor," *Eur. J. Cancer* 27: 765–770 (1991).

Y. Sawada et al., "Hemostatic Plug Formation in Normal and von Willebrand Pigs: The Effect of the Administration of Cryoprecipitate and a Monoclonal Antibody to Willebrand Factor," *Blood* 67: 1229–1239 (1986).

E. Ruoslahti & D. Pierschbacher, "New Perspectives in Cell Adhesion: RGD and Integrins," *Science* 238: 491–497 (1987).

L.De Marco et al., "Localization and Characterization of an α–Thrombin–binding Site on Platelet Glycoprotein Ibα," *J. Biol. Chem.* 283: 6478–6484 (1994).

H.R. Gralnick et al., "High–affinity α–Thrombin Binding to Platelet Glycoprotein Ibα: Identification of Two Binding Domains," *Proc. Natl. Acad. Sci. USA* 91:6334–6338 (1994).

H.R. Gralnick et al., "The Presence and Function of the Seven Transmembrane Thrombin Receptor on Bernard–Soulier Platelets," *Blood* 80:265a (1992).

J.Y.T. Lam et al., "Is Vasospasm Related to Platelet Deposition? Relationship in a Porcine Preparation of Arterial Injury in Vivo," *Circulation* 75: 243–248 (1987).

L.L. Thomsen et al., "Evidence for the Production of Nitric Oxide by Activated Macrophages Treated with Antitumo Agents Flavone–8–acetic acid and Xanthenone–4–acetic acid," *Cancer Res.* 50: 966–6970 (1990).

M.E. Watts et al., "Flavone Acetic Acid as a Modifier of Endothelial Cell Function," *Int. J. Radiat. Oncol. Biol. Phys* 22: 431–435 (1992).

D. Tousoulis et al., "Inhibition of Cyclic Flow Variations by von Willebrand Factor—Glycoprotein Ib Binding Domain," *Circulation* 93: 1255 (1996).

I.A. McGhie et al., "Abolition of Cyclic Flow Variations in Stenosed, Endothelium–Induced Coronary Arteries in Non-human Primates with a Peptide Fragment (VCL) Derived from Human Plasma von Willebrand Factor–Glycoprotein Ib Binding Domain," *Circulation* 90:2976–2981 (1994).

M. Murata et al., "Coronary Artery Disease and Polymorphisms in a Receptor Mediating Shear Stress–Dependent Platelet Activation," *Circulation* 96: 3281–3286 (1997).

USE OF FLAVONE 8-ACETIC ACID IN VASCULAR AND CARDIOVASCULAR INTERVENTIONS AND ACUTE CORONARY SYNDROMES

CROSS-REFERENCES

This application claims priority from Provisional application Ser. No. 60/178,008, by Jozef S. Mruk, filed Jan. 24, 2000, and entitled "Use of Flavone 8-Acetic Acid in Vascular and Cardiovascular Intervention and Acute Coronary Syndromes," the contents of which are hereby incorporated by this reference.

BACKGROUND OF THE INVENTION

This invention is directed to the use of flavone 8-acetic acid and its homologues in vascular and cardiovascular intervention and in acute coronary syndromes, alone or in combination with thrombolytic agents, antithrombotic agents, anticoagulants, or antiplatelet agents.

Vascular and cardiovascular diseases, including stroke, myocardial infarction, and blood clots, continue to be major causes of morbidity and mortality in the United States and other advanced industrial countries. A number of genetic and environmental factors have been linked to the occurrence of vascular and cardiovascular diseases, including genetic errors of lipid or lipoprotein metabolism and lifestyle factors such as tobacco smoking, the consumption of foods high in saturated fat, and lack of exercise. Despite a number of recent advances in the diagnosis and treatment of such diseases, they are still among the leading causes of death in the United States.

Therefore, there is a need for improved treatments for vascular and cardiovascular diseases. There is a particular need for agents and treatments that can treat both thrombosis and vasoconstriction in a coordinated manner.

SUMMARY

The administration of a flavone 8-carboxylic acid is effective in treating vascular and cardiovascular conditions and acute coronary syndromes.

In particular, one aspect of a method according to the present invention comprises a method for treating a vascular or cardiovascular condition or acute coronary syndromes comprising administering an effective amount of a flavone 8-carboxylic acid of formula (I)

(I)

where n is an integer from 1 to 3 to a mammal suffering from a vascular or cardiovascular condition or acute coronary syndromes.

Preferably, the flavone 8-carboxylic acid is flavone 8-acetic acid, in which n is 1.

The mammal can be a human or a socially or economically important nonhuman animal.

The flavone 8-carboxylic acid can act by reducing thrombosis or by reducing vasoconstriction.

Another aspect of the present invention is a method for treating a vascular or cardiovascular condition or acute coronary syndromes comprising administering an effective amount of a flavone 8-carboxylic acid of formula (I) where n is an integer from 1 to 3 and an additional agent that can ameliorate a vascular or a cardiovascular condition or acute coronary syndromes to a mammal suffering from a vascular or cardiovascular condition or acute coronary syndromes.

The additional agent can be selected from the group consisting of a thrombolytic agent, an antithrombotic agent, an anticoagulant, or an antiplatelet agent.

Thrombolytic agents include streptokinase, tissue plasminogen activator (tPA), and urokinase and modifications or derivatives of these molecules. Aminocaproic acid is an antithrombotic agent. Anticoagulants include heparin, warfarin, dicoumarol, phenprocoumon, acenocoumarol, ethyl biscoumacetate, and anisindione. Antiplatelet agents include aspirin, dipyramidole, ticlopidine, and plavix.

Yet another aspect of the present invention is a pharmaceutical composition comprising:

(1) an effective amount of a flavone 8-carboxylic acid of formula (I) where n is an integer from 1 to 3; and (2) a pharmaceutically acceptable carrier, the pharmaceutical composition being formulated for the treatment of a vascular or cardiovascular condition or acute coronary syndromes.

BRIEF DESCRIPTION OF THE DRAWINGS

These and other features, aspects, and advantages of the present invention will become better understood with reference to the following description, appended claims, and accompanying drawings where:

DETAILED DESCRIPTION

I have unexpectedly found that flavone-8-carboxylic acids of structure (I)

(I)

where n is an integer from 1 to 3 are useful in vascular and cardiovascular intervention and in treating acute coronary syndromes, alone or in combination with thrombolytic agents, antithrombotic agents, anticoagulants, or antiplatelet agents.

When n is 1, the resulting compound is flavone-8-acetic acid. When n is 2, the resulting compound is flavone-8-propionic acid. When n is 3, the resulting compound is flavone 8-butyric acid. As detailed below, the use of flavone-8-acetic acid (FAA) is typically preferred in methods according to the present invention, either alone or in combination with other agents.

Flavone 8-carboxylic acids and related compounds are described in U.S. Pat. No. 2,897,211 to da Re, U.S. Pat. No. 2,921,070 to da Re, U.S. Pat. No. 3,812,156 to Bonola et al., U.S. Pat. No. 4,057,641 to Appleton et al., U.S. Pat. No. 4,122,200 to Briet et al., U.S. Pat. No. 4,602,034 to Briet et al., U.S. Pat. No. 4,783,533 to Briet et al., U.S. Pat. No. 4,791,136 to Batchelor et al., U.S. Pat. No. 4,904,690 to Aono et al., U.S. Pat. No. 5,061,488 to Wiltrout et al., U.S. Pat. No. 5,096,707 to Wiltrout et al., U.S. Pat. No. 5,118,694 to Attwood et al., U.S. Pat. No. 5,126,129 to Wiltrout et al., U.S. Pat. No. 5,238,954 to Aristoff, and U.S. Pat. No. 5,756,538 to Cassels et al., all of which are incorporated herein in their entirety by this reference.

I. Use of Flavone 8-Carboxylic Acid Alone

One method according to the present invention is a method of use of a flavone 8-carboxylic acid of formula (I) wherein n is an integer from 1 to 3 alone in treating a vascular or a cardiovascular condition or acute coronary syndromes. This method comprises administering an effective amount of a flavone 8-carboxylic acid of formula (I) wherein n is an integer from 1 to 3 to a mammal suffering from a vascular or a cardiovascular condition or acute coronary syndromes. Preferably the flavone 8-carboxylic acid is flavone 8-acetic acid, wherein n is 1. The term "effective amount" is defined herein as an amount of the flavone 8-carboxylic acid that causes a detectable change in a parameter of clinical significance such as vasoconstriction or thrombosis. The mammal can be a human or a socially or environmentally significant nonhuman mammal such as a cow, a dog, a cat, a horse, a sheep, or a pig. The method of the present invention is not limited to humans.

The dosages to be administered can be determined by one of ordinary skill in the art depending on the clinical severity of the disease, the age and weight of the patient, the exposure of the patient to conditions that may affect the course of cardiovascular disease, and other pharmacokinetic factors generally understood in the art, such as liver and kidney metabolism. The interrelationship of dosages for animals of various sizes and species and humans based on mg/m$^3$ of surface area is described by E. J. Freireich et al., "Quantitative Comparison of Toxicity of Anticancer Agents in Mouse, Rat, Hamster, Dog, Monkey and Man," *Cancer Chemother. Rep.* 50: 219–244 (1966). Adjustments in the dosage regimen can be made to optimize the therapeutic response. Doses can be divided and administered on a daily basis or the dose can be reduced proportionally depending on the therapeutic situation.

The flavone 8-carboxylic acid can be administered orally or by other conventional routes of administration, such as intravenously, intraperitoneally, intramuscularly, transdermally, or by other routes.

As indicated above, a particularly preferred flavone 8-carboxylic acid is flavone 8-acetic acid.

The flavone 8-carboxylic acid can be administered as a pharmaceutical formulation in combination with pharmaceutically acceptable excipients and carrier materials such as inert solid diluents, aqueous solutions or non-toxic organic solvents. If desired, these pharmaceutical formulations may also contain preservatives and stabilizing agents and the like, as well as minor amounts of auxiliary substances such as wetting or emulsifying agents, as well as pH buffering agents and the like which enhance the effectiveness of the active ingredient. The pharmaceutically acceptable carrier can be chosen from those generally known in the art, including, but not limited to, human serum albumin, ion exchangers, dextrose, alumina, lecithin, buffer substances such as phosphate, glycine, sorbic acid, potassium sorbate, propylene glycol, polyethylene glycol, and salts or electrolytes such as protamine sulfate, sodium chloride, or potassium chloride. Other carriers can be used.

The flavone 8-carboxylic acid can act by reducing thrombosis or by reducing vasoconstriction, or by a combination of both mechanisms.

II. Use of Flavone 8-Carboxylic Acid Together With Other Agents

Another aspect of the present invention is a method of use of a flavone 8-carboxylic acid together with one or more additional agents in treating a vascular or a cardiovascular condition or acute coronary syndromes. This method comprises administering an effective amount of: (1) a flavone 8-carboxylic acid of formula (I) wherein n is an integer from 1 to 3 and (2) an additional agent that can ameliorate a vascular or a cardiovascular condition or acute coronary syndromes to a mammal suffering from a vascular or a cardiovascular condition or acute coronary syndromes. The amount of the flavone 8-carboxylic acid that is an effective amount is determined as described above. The amount of the additional agent that is an effective amount is an amount of the additional agent that causes a detectable change in a parameter of clinical significance such as vasoconstriction or thrombosis. More than one additional agent can be used. The additional agent can be, but is not necessarily limited to, a thrombolytic agent, an antithrombotic agent, an anticoagulant, or an antiplatelet agent.

As indicated above, the flavone 8-carboxylic acid is preferably flavone 8-acetic acid, in which n is 1.

As indicated above, the mammal can be a human or a nonhuman mammal.

Thrombolytic agents are well known in the art. They include streptokinase, tissue plasminogen activator (tPA), and urokinase, as well as modifications and derivatives of these molecules.

Antithrombotic agents are also well known in the art. They include aminocaproic acid.

Anticoagulants are also well known in the art. They include heparin, warfarin, dicoumarol, phenprocoumon, acenocoumarol, ethyl biscoumacetate, and anisindione.

Antiplatelet agents are also well known in the art. They include aspirin, dipyramidole, ticlopidine, and plavix.

The doses, frequencies of administrations, and routes of administration of these additional agents can be determined by principles generally known in the art. These principles are analogous to the principles that are described above for the administration of flavone 8-carboxylic acids. Similarly, formulations for the administration of these additional agents can be determined by principles well known in the art and analogous to the formulations suitable for the administration of flavone 8-carboxylic acids, paying due heed to the individual chemical characteristics of each additional agent.

III. Pharmaceutical Compositions

An additional aspect of the present invention is a pharmaceutical composition. A pharmaceutical composition according to the present invention is formulated for the treatment of a vascular or cardiovascular condition or acute coronary syndromes.

A pharmaceutical composition according to the present invention comprises: (1) an effective amount of a flavone 8-carboxylic acid of formula (I) wherein n is an integer from 1 to 3 as described above; and (2) a pharmaceutically acceptable carrier. The pharmaceutically acceptable carrier can be chosen from those generally known in the art, including, but not limited to, human serum albumin, ion exchangers, alumina, lecithin, buffered substances such as phosphate, glycine, sorbic acid, potassium sorbate, and salts or electrolytes such as protamine sulfate. Other carriers can be used.

Preferably, the flavone 8-carboxylic acid in the pharmaceutical composition is flavone 8-acetic acid, in which n is 1.

The invention is illustrated by the following Example. The Example is for exemplification only and is not intended to limit the invention.

EXAMPLE

Effect of Treatment with FAA on Thrombosis and Vasoconstriction in Pigs

Introduction

Von Willebrand factor (vWF) is necessary for normal platelet adhesion over an area of damaged vessel wall as for platelet—platelet interaction (aggregation) under high shear flow conditions. (J. Hawiger et al., "Platelet-Receptor Mechanisms for Adhesive Macromolecules" in *Interactions of Platelets with the Vessel Wall* (American Physiological Society, Bethesda, Md., 1985), pp. 1–19; J. Hawiger, "Formation and Regulation of Platelet and Fibrin Hemostatic Plug," *Hum. Pathol.* 18: 111–122 (1987); D. R Philips et al., "The Platelet Membrane Glycoprotein IIb–IIIa Complex," *Blood* 71: 831–843 (1988); M. H. Kroll & A. I. Schafer, "Biochemical Mechanisms of Platelet Activation," *Blood* 74: 1181–1195 (1989); P. S. Frenette & D. D. Wagner, "Molecular Medicine: Adhesion Molecules—Part I," *New. Eng. J. Med.* 334: 1526–1529 (1996); P. S. Frenette & D. D. Wagner, "Adhesion Molecules—Part II. Blood Vessels and Blood Cells," *New Eng. J. Med.* 335: 43–45 (1996); J. Lefkovits & E. J. Topol, "The Clinical Role of Platelet Glycoprotein IIb/IIIa Receptor Inhibitors in Ischemic Heart Disease," *Cleve. Clin. J. Med.* 63: 181–189 (1996); R. C. Becker, "Antiplatelet Therapy," *Science & Medicine* 3: 12–22 (1996); Z. Ruggeri, "Mechanisms Initiating Platelet Thrombus Formation," *Thrombosis & Hemostatis* 78: 611–616 (1997)). These interactions involve the platelet membrane glycoprotein (GP) complexes Ib-α and IIb–IIIa, and also fibrinogen, fibrin, and vitronectin. (J. Hawiger et al., "Platelet-Receptor Mechanisms for Adhesive Macromolecules" in *Interactions of Platelets with the Vessel Wall* (American Physiological Society, Bethesda, Md., 1985), pp. 1–19; J. Hawiger, "Formation and Regulation of Platelet and Fibrin Hemostatic Plug," *Hum. Pathol.* 18: 111–122 (1987); D. R Philips et al., "The Platelet Membrane Glycoprotein IIb–IIIa Complex," *Blood* 71: 831–843 (1988); M. H. Kroll & A. I. Schafer, "Biochemical Mechanisms of Platelet Activation," *Blood* 74: 1181–1195 (1989); P. S. Frenette & D. D. Wagner, "Molecular Medicine: Adhesion Molecules—Part I," *New. Eng. J. Med.* 334: 1526–1529 (1996); P. S. Frenette & D. D. Wagner, "Adhesion Molecules—Part II. Blood Vessels and Blood Cells," *New Eng. J. Med.* 335: 43–45 (1996); J. Lefkovits & E. J. Topol, "The Clinical Role of Platelet Glycoprotein IIb/IIIa Receptor Inhibitors in Ischemic Heart Disease," *Cleve. Clin. J. Med.* 63: 181–189 (1996); R. C. Becker, "Antiplatelet Therapy," *Science & Medicine* 3: 12–22 (1996); Z. Ruggeri, "Mechanisms Initiating Platelet Thrombus Formation," *Thrombosis & Hemostatis* 78: 611–616 (1997)).

Flavone-8-acetic acid (FAA; Flavonoid) (J. P. Armand et al., "Flavonoids: A New Class of Anticancer Agents? Preclinical and Clinical Data of Flavone Acetic Acid" in *Plant Flavonoids in Biology and Medicine II: Biochemical Cellular, and Medicinal Properties, pp.* 235–241; D. J. Kerr & S. B. Kaye, "Flavone Acetic Acid—Preclinical and Clinical Activity," *Eur. J. Cancer Clin. Oncol.* 25: 1271–1272 (1989)) is an adjuvant antitumor drug which inhibits implantation of solid tumors in the mouse, but also inhibits ristocetin-induced, von Willebrand factor-dependent platelet aggregation in humans (J. Rubin et al., "Flavone-8-Acetic Acid Inhibits Ristocetin-Induced Platelet Agglutination and Prolongs Bleeding Time," *Lancet* 2: 1081–1082 (1987)). This may cause a profound reduction in platelet-rich+arterial thrombosis after deep arterial injury. In Phase II clinical studies in humans, no clinically significant toxicity was observed. Thus the effect of FAA, at the maximal dose tolerated by humans (J. P. Armand et al., "Flavonoids: A New Class of Anticancer Agents? Preclinical and Clinical Data of Flavone Acetic Acid" in *Plant Flavonoids in Biology and Medicine II: Biochemical Cellular, and Medicinal Properties, pp.* 235–241; D. J. Kerr & S. B. Kaye, "Flavone Acetic Acid—Preclinical and Clinical Activity," *Eur. J. Cancer Clin. Oncol.* 25: 1271–1272 (1989); J. Rubin et al., "Flavone-8-Acetic Acid Inhibits Ristocetin-Induced Platelet Agglutination and Prolongs Bleeding Time," *Lancet* 2: 1081–1082 (1987)), on platelet-dependent thrombosis was studied in vivo in the deeply injured porcine carotid artery produced by balloon angioplasty as a model of mainly GP Ib inhibition.

METHODS

Twenty normal pigs of Babcock 4-way cross stock (a mixture of Landrace, Yorkshire, Hampshire, and Durock breeds) approximately 4 months old with a mean weight of 40±1 kg (approximately 1 $m^2$ body surface area) (P. L. Altman & D. S. Dittmer, "Metabolism" in *Biological Handbooks* (Federation of American Societies for Experimental Biology, Bethesda, Md., 1968), pp. 346–348), were obtained from local farmers. They were randomly assigned to treatment with either placebo (0.9% saline) or FAA (National Cancer Institute), administered as a bolus of 5.5 $g/m^2$ followed immediately by an infusion at 0.14 $g/m^2$/minute. Loading dose and maintenance infusion were calculated based on preliminary pharmacokinetic experiments in pigs. Monoexponential declines in plasma concentration of FAA were fitted to the equation $C=Ae^{-\alpha t}$, where A is the intercept at t=0, and α is the elimination rate constant. A weighing factor of 1/C, where C is the plasma concentration of FAA at time t, was employed.

Drug administration during the balloon dilatation procedure was not blinded, but all subsequent tissue and sample analysis was performed without knowledge of the treatment administered. This study was approved by the Mayo Clinic Animal Care Committee and conformed to American Heart Associated guidelines.

Experimental Protocol

The model of deep arterial injury in the porcine carotid artery has been described in detail previously (P. M. Steele et al., "Balloon Angioplasty: Natural History of the Pathophysiologic Response to Injury in a Pig Model," *Cir. Res.* 57: 105–112 (1985); M. Heras et al., "Hirudin, Heparin, and Placebo During Deep Arterial Injury in the Pig. The in Vivo Role of Thrombin in Platelet-Mediated Thrombosis," *Circulation* 82: 1476–1484 (1990); J. Y. T. Lam et al., "Is Vasospasm Related to Platelet Deposition? Relationship in a Porcine Preparation of Arterial Injury in Vivo," *Circulation* 75: 243–248 (1987)). Autologous platelets were labeled with 300 $\mu$Cu of $^{111}$Indium-tropolone and reinjected together with 250 $\mu$Cu of $^{125}$Iodine-labeled porcine fibrinogen on the day prior to the procedure M. Heras et al., "Hirudin, Heparin, and Placebo During Deep Arterial Injury in the Pig. The in Vivo Role of Thrombin in Platelet-Mediated Thrombosis," *Circulation* 82: 1476–1484 (1990); J. Y. T. Lam et al., "Is Vasospasm Related to Platelet Deposition? Relationship in a Porcine Preparation of Arterial Injury in Vivo," *Circulation* 75: 243–248 (1987); J. Mruk et al., "Does Anti-Thrombotic Therapy Influence Residual Thrombus After Thrombolysis of Platelet-Rich Thrombus?," *Circulation* 93: 792–799 (1996)). On the day of surgery, the pigs were sedated with 1 g intramuscular ketamine (Ketaset, Bristol Laboratories, Syracuse, N.Y.), intubated and mechanically ventilated with room air (Harvard respirator, Harvard Apparatus, South Natick, Mass.). Anesthesia was maintained with a continuous infusion of etomidate (Abbott Laboratories, North Chicago, Ill.) 40 mg/l, fentanyl (Elkins-Sinn, Inc., Cherry Hill, N.J.) 10 mg/l, and ketamine 1,000 mg/l, at about 5 ml/minute. The ECG and intra-arterial pressure were continuously monitored throughout the procedure.

The left femoral vein and artery and the right femoral vein were dissected. A 9 F sheath was placed in the left femoral artery, and 14 gauge angiocaths were inserted in the left and right femoral veins. Blood for platelet count, fibrinogen, hematocrit, activated partial thromboplastin time (aPTT), and FAA levels was obtained from the right femoral vein. All the lines for blood sampling were continuously flushed with 0.9% saline. After all the lines were in place, a basal bleeding time was performed in the ear using a standardized method (Y. Sawada et al., "Hemostatic Plug Formation in Normal and von Willebrand Pigs: The Effect of the Administration of Cryoprecipitate and a Monoclonal Antibody to Willebrand Factor," *Blood* 67: 1229–1239 (1986). The normal saline treatment bolus, or FAA was then given and followed immediately by the infusion administered via the left femoral vein with a Harvard pump (Harvard Apparatus, South Natick, Mass.) at the rate of 0.8 ml/minute. Thirty minutes after starting the infusions another bleeding time was performed.

An 8 mm×3 cm polyethylene angioplasty catheter (Blue Max, Medi-tech, Watertown, Mass.) was advanced under fluoroscopic guidance to the left and then to the right common carotid arteries for arterial dilatation. Angioplasty was performed 30 minutes after starting treatment, between the first and third cervical vertebrae, using a standardized procedure (5 inflations of 30 seconds duration at 7 atmospheres, with 60 seconds between inflations). Carotid angiography was performed by injecting 6 ml of ionic contrast material (Renografin 76, Squibb, Princeton, N.J.) just prior to carotid dilatation, using a catheter (8 F) with a metal ring of known dimension (Cordis Corporation, Miami, Fla.). Spot films were also taken during balloon dilatation. After the series of 5 inflations the balloon catheter was withdrawn to the proximal carotid artery and angiography was repeated.

Fifteen minutes after dilatation of the right carotid artery, 120 ml of 0.5% Evans blue in 0.9% saline was injected into the descending aorta to demarcate the extent of arterial injury. Animals then received an overdose of pentobarbital and were euthanized. The proximal descending aorta was immediately cannulated and the carotid arteries perfused with buffered 0.9% saline until eluent from the external jugular veins was clear. The vessels were then perfused with buffered 2% glutaraldehyde for 15 minutes. All perfusions were at physiologic pressure. After fixation situ, the carotid arteries were harvested and cleaned of all adventitia. The dilated portions were divided into 2 equal segments and 2 similar-sized segments were taken proximal and distal to the dilated areas (P. M. Steele et al., "Balloon Angioplasty: Natural History of the Pathophysiologic Response to Injury in a Pig Model," *Cir. Res.* 57: 105–112 (1985); M. Heras et al., "Hirudin, Heparin, and Placebo During Deep Arterial Injury in the Pig. The in Vivo Role of Thrombin in Platelet-Mediated Thrombosis," *Circulation* 82: 1476–1484 (1990); J. Y. T. Lam et al., "Is Vasospasm Related to Platelet Deposition? Relationship in a Porcine Preparation of Arterial Injury in Vivo," *Circulation* 75: 243–248 (1987)).

Tissue Analysis

Platelet and fibrin(ogen) deposition on the arterial segments were quantified by the method of Dewanjee et al. (J. Mruk et al., "Does Anti-Thrombotic Therapy Influence Residual Thrombus After Thrombolysis of Platelet-Rich Thrombus?," *Circulation* 93: 792–799 (1996); M. K. Dewanjee et al., "Methods of Assessment of Thrombosis in Vivo," *Ann. N.Y. Acad. Sci.* 516: 541–571 (1987); M. K. Dewanjee et al., "Quantification of Platelet Retention in Aortocoronary Femoral Vein Bypass Graft in Dogs Treated with Dipyramidole and Aspirin," *Circulation* 69: 350–356 (1984)). Counting for $^{111}$Indium was performed on the day of surgery, and for $^{125}$Iodine 2 to 3 weeks later after the Indium had decayed.

The extent of deep arterial injury (defined as a tear through the internal elastic lamina into the arterial media) in the dilated portion of the vessel was assessed histologically as previously described (P. M. Steele et al., "Balloon Angioplasty: Natural History of the Pathophysiologic Response to Injury in a Pig Model," *Cir. Res.* 57: 105–112 (1985); M. Heras et al., "Hirudin, Heparin, and Placebo During Deep Arterial Injury in the Pig. The in Vivo Role of Thrombin in Platelet-Mediated Thrombosis," *Circulation* 82: 1476–1484 (1990); J. Y. T. Lam et al., "Is Vasospasm Related to Platelet Deposition? Relationship in a Porcine Preparation of Arterial Injury in Vivo," *Circulation* 75: 243–248 (1987)). Each segment was cut open, pinned and color photographed. Computer-assisted planimetric measurements of the area of deep injury and the total segment area were then obtained. The presence of macroscopic mural thrombosis was assessed using a 2-fold magnifying glass.

Vasoconstriction

The severity of localized vasoconstriction was determined immediately distal to the dilatation site from angiograms of the common carotid arteries obtained before and after the dilatation procedure. Computer-assisted planimetry was used to measure the mean maximal narrowing in lumen diameter before and after the procedure, expressed as a percentage of the respective arterial dimension before dilatation (J. Y. T. Lam et al., "Is Vasospasm Related to Platelet Deposition? Relationship in a Porcine Preparation of Arterial Injury in Vivo," *Circulation* 75: 243–248 (1987)).

Laboratory Tests

All blood samples were collected with the 2-syringe technique (0.13 M trisodium citrate as anticoagulant; anticoagulant:blood=1:10). Samples for platelet count, fibrinogen, hematocrit, aPTT, and FAA concentration were drawn before drug administration, 30 minutes after starting the infusions and immediately before euthanasia. Platelet count, hematocrit, aPTT, and fibrinogen were determined using standard laboratory methods (Mayo Clinic, Clinical Laboratories). Blood for FAA levels was mixed 9 parts to 1 with 0.13 M trisodium citrate solution, centrifuged to obtain plasma and stored at −70° C. Assays were performed as a single batch. The method of determination of FAA in plasma was that of L. Malspeis (personal communication). Briefly, plasma (0.25–0.50 ml) was diluted to 1 ml with 0.5 ml of 0.5 M sodium acetate (pH 3.0) and normal saline. After addition of diethyl ether (4 ml) tubes were shaken on a mechanical shaker for 15 minutes. Following low speed centrifugation, the ether phase was evaporated to dryness under a stream of nitrogen and the residue dissolved in mobile solvent prior to HPLC analysis. Samples were analyzed by reversed-phase HPLC on an IBM $C_{18}$ (10 micron) column with a mobile solvent of methanol/water mixture. Detection was by UV absorbance at 254 nm. Standard curves were prepared by adding known amounts of FAA to blood blank plasma and analyzing as described above. Concentrations of FAA were determined by fitting unknown sample peak areas to equations derived from standard curves.

Statistical Methods

Results are presented as mean±SEM. Two dilated segments per artery per animal were analyzed. Because of the variability of platelet and fibrin(ogen) deposition and to use the animal as the unit of study (since all segments in the pig were exposed to the same treatment), analysis was performed on the natural logarithm of these values (per $cm^2$ of total area) averaged over all deeply injured segments. Treated and control groups were then compared using the Student's t-test for continuous variables. Pearson's Chi-Square test was used to test for a difference between groups in the incidence of mural thrombus.

RESULTS

Figure 1A:
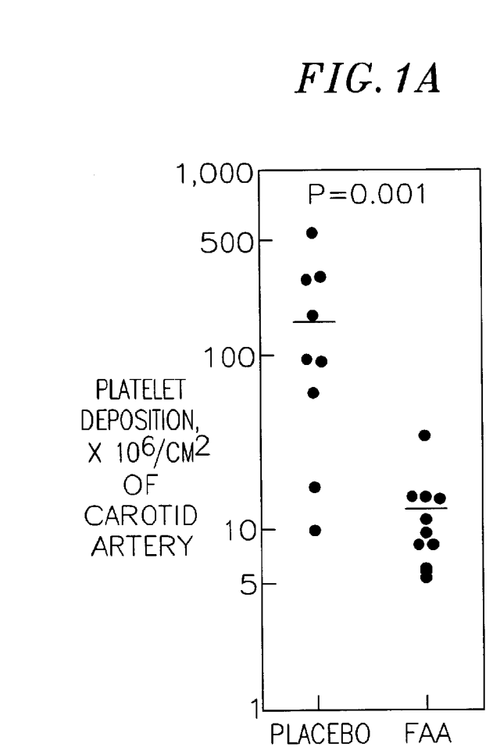
FIG. 1(a) is a graph showing the effect of the administration of flavone 8-acetic acid (FAA) on platelet deposition ($\times 10^6/cm^2$ of carotid artery); left panel, placebo; right panel, FAA.
Figure 1B:
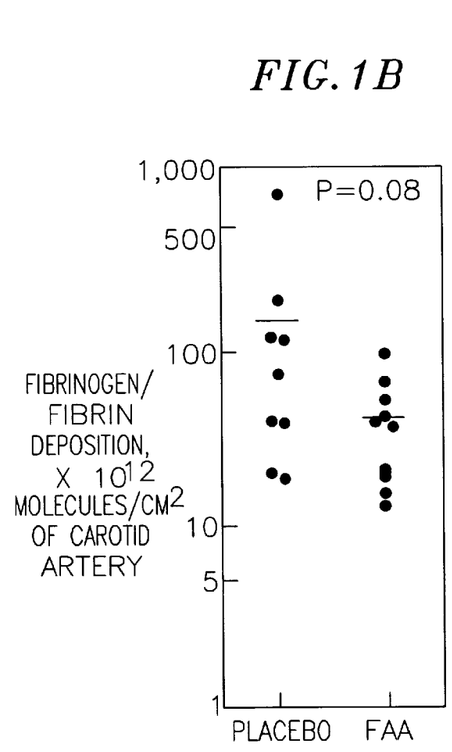
FIG. 1(b) is a graph showing the effect of the administration of FAA on fibrinogen/fibrin deposition ($\times 10^{12}$ molecules/$cm^2$ of carotid artery); left panel, placebo; right panel, FAA.
Figure 1C:
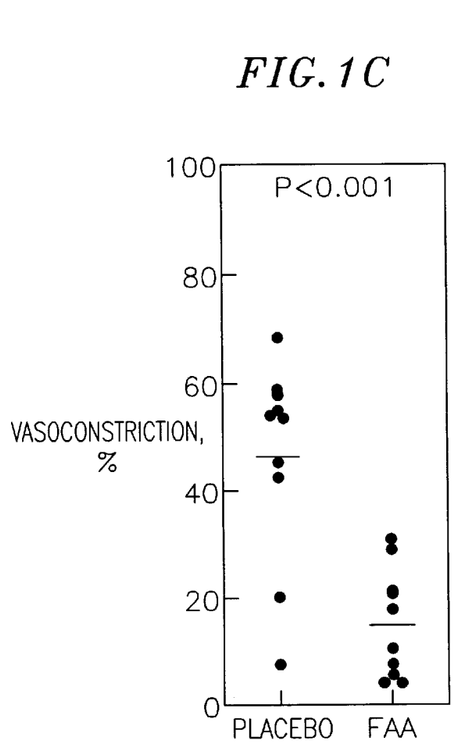
FIG. 1(c) is a graph showing the effect of administration of FAA on vasoconstriction in percent; left panel, placebo; right panel, FAA.

Platelet and fibrin(ogen) deposition (FIG. 1): Deep arterial injury occurred in 70% of segments in the dilated region; the remainder had subendothelial injury. Platelet deposition in deeply injured segments in animals treated with FAA was more than 12-fold lower than those treated with placebo (13±3 vs. 164±51×$10^6$/$cm^2$, p=0.001). Fibrin(ogen) deposition was similar but slightly less in treated animals (40±8 vs. 140±69×$10^{12}$ molecules/$cm^2$, p=0.08 (FIG. 1)).

Mural thrombus: Large macroscopic mural thrombi were present in all pigs treated with placebo. FAA produced a reduction in the incidence and size of thrombus formation. Very small mural thrombi occurred in 40% of treated pigs (p=0.005). There were large thrombi in 85% of the deeply injured segments in the placebo group and very small thrombi in 30% of the treated group.

Figure 2:
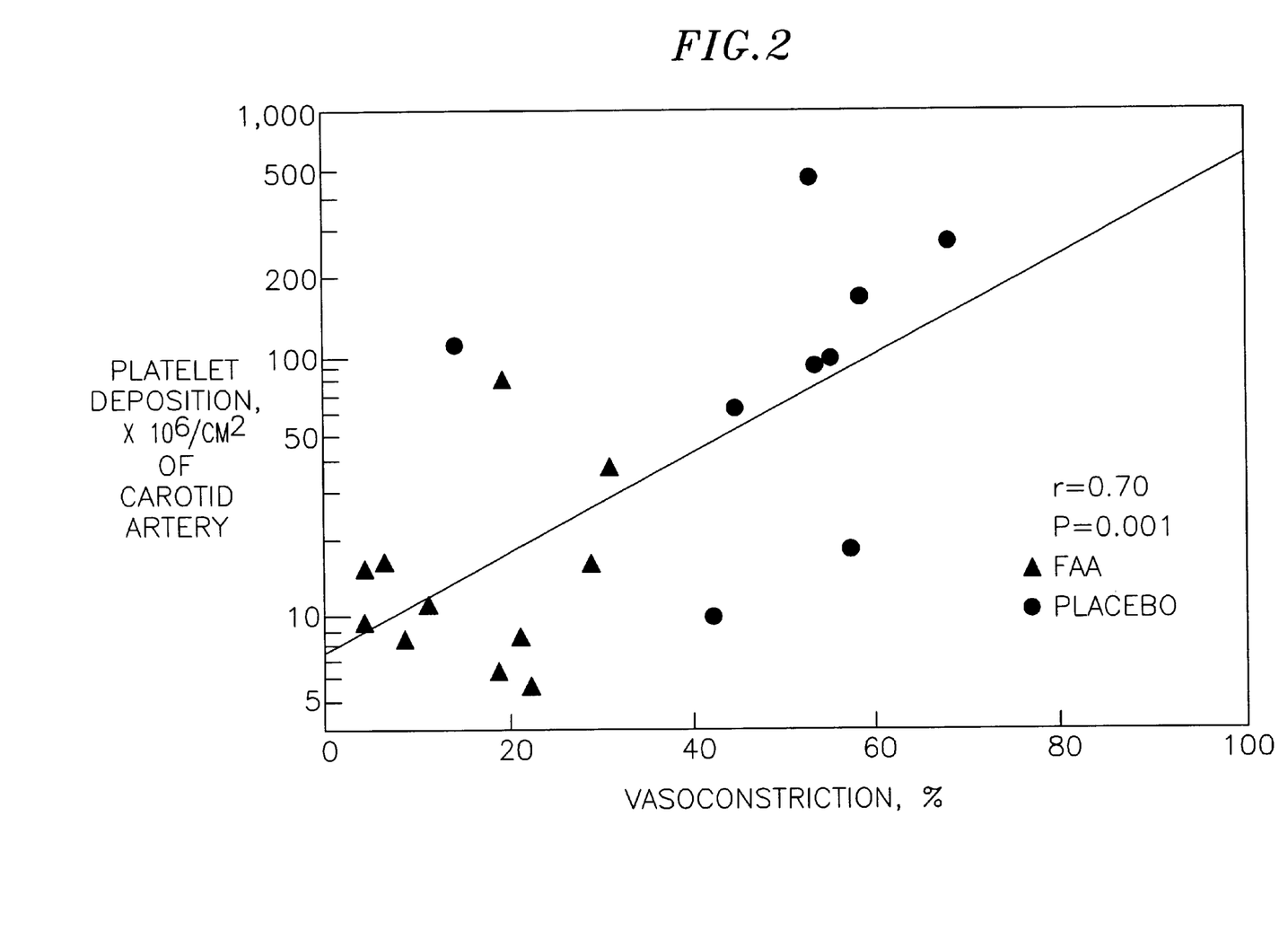
FIG. 2 is a graph showing the correlation between platelet deposition (Y-axis; $\times 10^6/cm^2$ of carotid artery) and vasoconstriction in percent (X-axis) after administration of FAA or a placebo (▲, FAA; ●, placebo)
Figure 3:
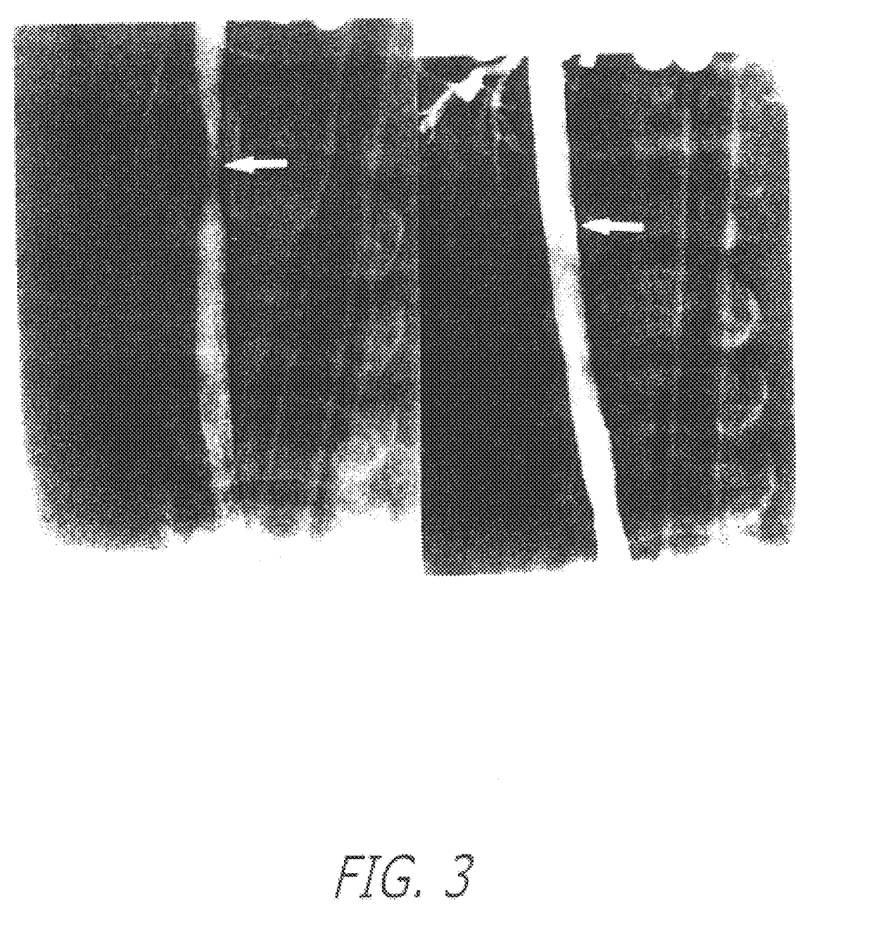
FIG. 3 is a photomicrograph showing vasoconstriction immediately distal to dilated segment (arrow) in a placebo (left panel) and FAA-treated (right panel) pig.

Vasoconstriction (FIGS. 1, 2 and 3): Vasoconstriction immediately distal to the area of dilatation was significantly greater in the placebo group than in FAA-treated animals (46±6% versus 15±3%, p<0.001), FIGS. 1 and 2.

FAA Pharmacokinetics: Plasma elimination of FAA in two animals administered with an intravenous bolus dose of 1 gm/$m^2$ was fitted to a one compartment open model. Plasma half-life and plasma clearance values were 27.9 minutes and 279 ml/min/$m^2$, respectively. The intravenous bolus and continuous infusion doses to maintain a plasma concentration of 500 μg/ml calculated from these values, were 5.5 gm/$m^2$ and 140 mg/min/$m^2$, respectively.

Laboratory tests: The plasma level of FAA prior to angioplasty was 515±23 μg/ml; at the end of the procedure it was 575±36 μg/ml. The aPTT was only slightly increased in the treated animals (1.0 to 1.2×baseline), but the bleeding time in the 5 animals in which it was measured increased from 157±29 seconds to 522±123 seconds. In 4 of the animals the bleeding time was prolonged more than 210 seconds (2 standard deviations above the mean laboratory value) after the administration of FAA.

DISCUSSION

This study demonstrates that platelet-dependent thrombus formation following deep arterial injury by balloon dilatation is profoundly reduced by FAA (Flavonoid) which appears to block vWF platelet glycoprotein Ibα-dependent platelet aggregation. This suggests that this mechanism of antithrombotic therapy may be clinically useful. A dosage of FAA was evaluated in the upper therapeutic range in humans as assessed by plasma concentrations (J. P. Armand et al., "Flavonoids: A New Class of Anticancer Agents? Preclinical and Clinical Data of Flavone Acetic Acid" in *Plant Flavonoids in Biology and Medicine II: Biochemical Cellular, and Medicinal Properties, pp.* 235–241; D. J. Kerr & S. B. Kaye, "Flavone Acetic Acid—Preclinical and Clinical Activity," *Eur. J. Cancer Clin. Oncol.* 25: 1271–1272 (1989); J. Rubin et al., "Flavone-8-Acetic Acid Inhibits Ristocetin-Induced Platelet Agglutination and Prolongs Bleeding Time," *Lancet* 2: 1081–1082 (1987)). Platelet deposition and the incidence of mural thrombosis in pigs treated with FAA was significantly lower than those treated with placebo. Fibrin(ogen) deposition was similar and not significantly decreased by FAA compared to placebo.

FAA is an adjuvant antitumor agent, which inhibits implantation of solid tumors in mice, by an unknown mechanism (J. P. Armand et al., "Flavonoids: A New Class of Anticancer Agents? Preclinical and Clinical Data of Flavone Acetic Acid" in *Plant Flavonoids in Biology and Medicine II: Biochemical Cellular, and Medicinal Properties, pp.* 235–241; D. J. Kerr & S. B. Kaye, "Flavone Acetic Acid—Preclinical and Clinical Activity," *Eur. J. Cancer Clin. Oncol.* 25: 1271–1272 (1989); J. Rubin et al., "Flavone-8-Acetic Acid Inhibits Ristocetin-Induced Platelet Agglutination and Prolongs Bleeding Time," *Lancet* 2: 1081–1082 (1987)). Prolonged treatment causes reduced blood flow, which may lead to hemorrhagic necrosis of these tumors (G. P. Smith et al., "Flavone Acetic Acid (NSC 347512) Induces Hemorrhagic Necrosis of Mouse Colon 26 and 38 Tumors," *Eur. J. Cancer Clin. Oncol.* 23: 1209–1211 (1987); S. Hill et al., "Vascular Collapse After Flavone Acetic Acid: A Possible Mechanism of Its Anti-Tumor Action," *Eur. J. Cancer Clin. Oncol.* 25: 1419–1424 (1989)). It has also been shown that FAA produces intravascular coagulation in tumor-bearing mice (J. C. Murray et al., "Flavone Acetic Acid Induces a Coagulopathy in Mice," *Br. J. Cancer* 60: 729–733 (1989); G. Thurston et al., "Anticoagulant Treatment Does Not Action of Flavone Acetic Acid in Tumor-Bearing Mice," *Br. J. Cancer* 64: 689–692 (1991); J. C. Murray et al., "Selective Induction of Endothelial Cell Tissue Factor in the Presence of a Tumor-Derived Mediator: A Potential Mechanism of Flavone Acetic Acid Action in Tumor Vasculature," *Int. J. Cancer* 49: 254–259 (1991); J. C. Murray et al., "Flavone Acetic Acid Potentiates the Induction of Endothelial Procoagulant Activity by Tumor Necrosis Factor," *Eur. J. Cancer* 27: 765–770 (1991)). These changes are thought to be secondary to necrosis in the solid tumors.

Rubin et al. found that FAA administered to patients with cancer inhibited ristocetin-induced platelet aggregation (vWF-GP Ibα-dependent aggregation) and prolonged the bleeding time (J. Rubin et al., "Flavone-8-Acetic Acid Inhibits Ristocetin-Induced Platelet Agglutination and Prolongs Bleeding Time," *Lancet* 2: 1081–1082 (1987)). Ex vivo and in vitro platelet aggregation studies with human platelet-rich plasma showed that in the presence of FAA, aggregation induced by adenosine diphosphate (ADP), collagen, arachidonic acid, and adrenalin was not inhibited (J. Rubin et al., "Flavone-8-Acetic Acid Inhibits Ristocetin-Induced Platelet Agglutination and Prolongs Bleeding Time," *Lancet* 2: 1081–1082 (1987)). Plasma ristocetin cofactor activity was unchanged (J. Rubin et al., "Flavone-8-Acetic Acid Inhibits Ristocetin-Induced Platelet Agglutination and Prolongs Bleeding Time," *Lancet* 2: 1081–1082 (1987)).

Von Willebrand's factor interacts with human platelets through two different mechanisms (J. Hawiger et al., "Platelet-Receptor Mechanisms for Adhesive Macromolecules" in *Interactions of Platelets with the Vessel Wall* (American Physiological Society, Bethesda, Md., 1985), pp. 1–19; J. Hawiger, "Formation and Regulation of Platelet and Fibrin Hemostatic Plug," *Hum. Pathol.* 18: 111–122 (1987); P. S. Frenette & D. D. Wagner, "Molecular Medicine: Adhesion Molecules—Part I," *New. Eng. J. Med.* 334: 1526–1529 (1996); P. S. Frenette & D. D. Wagner, "Adhesion Molecules—Part II. Blood Vessels and Blood Cells," *New Eng. J. Med.* 335: 43–45 (1996)). Under high shear flow conditions, the vessel-wall bound vWF binds to the platelet glycoprotein Ib-α (GPIb-α) in the early phases of hemostasis (platelet adhesion), a process which is independent of ADP and is induced by ristocetin. The other interaction, of soluble von Willebrand's factor with platelets involves glycoprotein IIb–IIIa complex, exposed on activated platelets (platelet aggregation). This process requires ADP and $Ca^{++}$, and is not induced by ristocetin, in common with other adhesive proteins like fibrinogen, fibronectin, and probably with thrombospondin. Interactions of the glycoprotein IIb–IIIa complex, a member of a large family of related molecules known as integrins, with adhesive proteins involves the RDG (Arg-Gly-Asp) amino acid recognition sequence, necessary for platelet—platelet adhesion (platelet aggregation) (Y. Sawada et al., "Hemostatic Plug Formation in Normal and von Willebrand Pigs: The Effect of the Administration of Cryoprecipitate and a Monoclonal Antibody to Willebrand Factor," *Blood* 67: 1229–1239 (1986); E. Ruoslahti & D. Pierschbacher, "New Perspectives in Cell Adhesion: RGD and Integrins," *Science* 238: 491–497 (1987)). Interaction and binding of proteins to the glycoprotein Ib-α does not involve the RDG recognition sequence (J. Hawiger et al., "Platelet-Receptor Mechanisms for Adhesive Macromolecules" in *Interactions of Platelets with the Vessel Wall* (American Physiological Society, Bethesda, Md., 1985), pp. 1–19; J. Hawiger, "Formation and Regulation of Platelet and Fibrin Hemostatic Plug," *Hum. Pathol.* 18: 111–122 (1987)). The antithrombotic mode of action of flavone acetic acid (Flavonoid) remains unknown but aggregation studies with ristocetin and prolongation of the bleeding time in humans and in the study reported in this Example, suggest that flavone acetic acid interferes with platelets in the formation of the initial platelet hemostatic plug. This is probably achieved by inhibition of binding of von Willebrand's factor to its binding site on the platelet glycoprotein Ib-α.

It was recently discovered that thrombin binds with high affinity to platelet GP Ibα (L. De Marco et al., "Localization and Characterization of an α-Thrombin-binding Site on Platelet Glycoprotein Ibα," *J. Biol. Chem.* 283: 6478–6484 (1994); H. R. Gralnick et al., "High-affinity α-Thrombin Binding to Platelet Glycoprotein Ibα: Identification of Two Binding Domains," *Proc. Natl. Acad. Sci. USA* 91: 6334–6338 (1994)) Thrombin binding site on GP Ibα is distinct from, but in close proximity to, the one involved in binding of the adhesive protein, von Willebrand factor (L. De Marco et al., "Localization and Characterization of an α-Thrombin-binding Site on Platelet Glycoprotein Ib," *J. Biol. Chem.* 283: 6478–6484 (1994); H. R. Gralnick et al., "High-affinity α-Thrombin Binding to Platelet Glycoprotein Ibα: Identification of Two Binding Domains," *Proc. Natl. Acad. Sci. USA* 91: 6334–6338 (1994)). The proposed role of GP Ibα in thrombin binding includes acting as high-affinity receptor for bringing thrombin near the platelet surface (S. R. Couglin et al., "Characterization of a Functional Thrombin Receptor," *J. Clin. Invest.* 89: 351–355 (1992)). It was suggested that initiating event in thrombin-induced platelet activation occurs via the GP Ibα (H. R. Gralnick et al., "The Presence and Function of the Seven Transmembrane Thrombin Receptor on Bernard-Soulier Platelets," *Blood* 80: 265a (1992)).

FAA binding to von Willebrand factor site on GP Ibα, due to proximity, could partially cover high-affinity binding site for thrombin on GP Ibα. This could be another plausible explanation for the findings of this Example. FAA significantly decreased platelet deposition and macroscopic thrombosis (antiplatelet effect; solid-phase platelet GP Ibα), but did not have a significant effect on fibrin(ogen) deposition or prolongation of aPTT (no anticoagulant activity; there was no inhibitory effect on the action of thrombin on the soluble-phase fibrinogen).

During administration of FAA, vasoconstriction just distal to the site of dilatation was significantly reduced. It was previously shown that the degree of platelet deposition directly correlates with the degree of arterial vasoconstriction (J. Y. T. Lam et al., "Is Vasospasm Related to Platelet Deposition? Relationship in a Porcine Preparation of Arterial Injury in Vivo," *Circulation* 75: 243–248 (1987)). Whether the current reduced vasoconstriction relates mainly to platelet deposition or also to a direct action of FAA on the vessel wall, the endothelium, increased nitric oxide production or to some other mechanism, remains unclear at this point (J. Y. T. Lam et al., "Is Vasospasm Related to Platelet Deposition? Relationship in a Porcine Preparation of Arterial Injury in Vivo," *Circulation* 75: 243–248 (1987); L. L. Thomsen et al., "Evidence for the Production of Nitric Oxide by Activated Macrophages Treated with Antitumor Agents Flavone-8-acetic acid and Xantherone-4-acetic acid," *Cancer Res.* 50: 6966–6970 (1990); M. E. Watts et al., "Flavone Acetic Acid as a Modifier of Endothelial Cell Function," *Int. J. Radiat. Oncol. Biol. Phys.* 22: 431–435 (1992)).

In conclusion, complex mechanisms are involved in the formation of arterial thrombi. At dosages used in clinical practice FAA (Flavonoid) is an effective agent for reducing platelet-dependent thrombosis in vivo over areas of deep arterial injury. There may be a role for interaction of vWF and GP Ibα in acute ischemic coronary syndromes (D. Tousoulis et al., "Inhibition of Cyclic Flow Variations by von Willebrand Factor—Glycoprotein Ib Binding Domain," *Circulation* 93: 1255 (1996); I. A. McGhie et al., "Abolition of Cyclic Flow Variations in Stenosed, Endothelium-Induced Coronary Arteries in Non-Human Primates with a Peptide Fragment (VCL) Derived from Human von Willebrand Factor Glycoprotein Ib Binding Domain," *Circulation* 90: 2976–2981 (1994); M. Murata et al., "Coronary Artery Disease and Polymorphism in Receptor Mediating Shear Stress-Dependent Platelet Activation," *Circulation*

96: 3281–3286 (1997)) FAA also reduces the vasoconstriction associated with arterial balloon angioplasty probably related to the reduction in platelet deposition (J. Y. T. Lam et al., "Is Vasospasm Related to Platelet Deposition? Relationship in a Porcine Preparation of Arterial Injury in Vivo," *Circulation* 75: 243–248 (1987).

Potentially, FAA could be used for short periods (also has short plasma half-life) during vascular interventions, in combination with other anti-thrombotics/anti-coagulants, for primary prevention of platelet dependent thrombosis in the areas of deep arterial injury.

ADVANTAGES OF THE INVENTION

The present invention provides a new method of treating vascular and cardiovascular conditions and acute coronary syndromes. It operates both by reducing thrombosis and reducing vasoconstriction, thus providing exceptionally efficient treatment. It does not interfere with other treatment modalities and can be used in conjunction with them.

Although the present invention has been described in considerable detail, with reference to certain preferred versions thereof, other versions and embodiments are possible. Therefore, the scope of the invention is determined by the following claims.

I claim:

1. A method for treating a vascular or cardiovascular condition or acute coronary syndromes comprising administering an effective amount of a flavone 8-carboxylic acid of formula (I)

where n is an integer from 1 to 3 to a mammal suffering from a vascular or cardiovascular condition or acute coronary syndromes.

2. The method of claim 1 wherein the flavone 8-carboxylic acid is flavone 8-acetic acid.

3. The method of claim 1 wherein the mammal is a human.

4. The method of claim 1 wherein the mammal is a socially or economically important nonhuman mammal selected from the group consisting of a cow, a dog, a cat, a horse, a sheep, and a pig.

5. The method of claim 1 wherein the flavone 8-carboxylic acid acts by reducing thrombosis.

6. The method of claim 1 wherein the flavone 8-carboxylic acid acts by reducing vasoconstriction.

7. A method for treating a vascular or cardiovascular condition or acute coronary syndromes comprising administering an effective amount of a flavone 8-carboxylic acid of formula (I) where n is an integer from 1 to 3 and an additional agent that can ameliorate a vascular or a cardiovascular condition or acute coronary syndromes to a mammal suffering from a vascular or cardiovascular condition or acute coronary syndromes.

8. The method of claim 7 wherein the flavone 8-carboxylic acid is flavone 8-acetic acid.

9. The method of claim 7 wherein the mammal is a human.

10. The method of claim 7 wherein the mammal is a socially or economically important nonhuman animal selected from the group consisting of a cow, a dog, a cat, a horse, a sheep, or a pig.

11. The method of claim 7 wherein the flavone 8-carboxylic acid acts by reducing thrombosis.

12. The method of claim 7 wherein the flavone 8-carboxylic acid acts by reducing vasoconstriction.

13. The method of claim 7 wherein the additional agent is selected from the group consisting of a thrombolytic agent, an antithrombotic agent, an anticoagulant, or an antiplatelet agent.

14. The method of claim 13 wherein the additional agent is an antithrombotic agent.

15. The method of claim 14 wherein the antithrombotic agent is aminocaproic acid.

16. The method of claim 13 wherein the additional agent is an anticoagulant.

17. The method of claim 16 wherein the anticoagulant is selected from the group consisting of heparin, warfarin, dicoumarol, phenprocoumon, acenocoumarol, ethyl biscoumacetate, and anisindione.

18. The method of claim 13 wherein the additional agent is an antiplatelet agent.

19. The method of claim 18 wherein the antiplatelet agent is selected from the group consisting of aspirin, dipyramidole, ticlopidine, and plavix.

20. The method of claim 13 wherein the additional agent is a thrombolytic agent.

21. The method of claim 20 wherein the thrombolytic agent is selected from the group consisting of streptokinase, tissue plasminogen activator (tPA), urokinase, and modifications and derivatives of these molecules.

22. A pharmaceutical composition comprising:

(a) an effective amount of a flavone 8-carboxylic acid of formula (I) where n is an integer from 1 to 3; and (b) a pharmaceutically acceptable carrier, the pharmaceutical composition being formulated for the treatment of a vascular or cardiovascular condition or acute coronary syndromes.

23. The pharmaceutical composition of claim 22 wherein the flavone 8-carboxylic acid is flavone 8-acetic acid.

* * * * *